United States Patent [19]

Waldner et al.

[11] Patent Number: 4,748,244
[45] Date of Patent: May 31, 1988

[54] PROCESS FOR THE PREPARATION OF PYRIDINE-2-3-DICARBOXYLIC ACID DERIVATIVES, AND NOVEL 1-AMINO-1,4-DIHYDROPYRIDINE-2-3-DIARBOXYLIC ACID DERIVATIVES

[75] Inventors: Adrian Waldner, Allschwil; Achim Roloff, Rheinfelden; Daniel Bellus, Riehen, all of Switzerland

[73] Assignee: Ciba-Geigy Corporation, Ardsley, N.Y.

[21] Appl. No.: 730,026

[22] Filed: May 3, 1985

[30] Foreign Application Priority Data

May 11, 1984 [CH] Switzerland .................. 2337/84

[51] Int. Cl.⁴ ............ C07D 213/803; C07D 213/82; C07D 471/04; C07D 491/048
[52] U.S. Cl. .................... 544/313; 546/113; 546/116; 546/193; 546/194; 546/281; 546/291; 546/296; 546/297; 546/299; 546/306; 546/316; 546/321; 546/250
[58] Field of Search ............ 546/306, 296, 316, 297, 546/321, 291, 113, 299, 116, 193, 281, 194, 250; 544/313

[56] References Cited

U.S. PATENT DOCUMENTS 3,027,380 3/1962 Leonard et al. .................. 546/321
4,439,607 3/1984 Drabb .............................. 546/116

FOREIGN PATENT DOCUMENTS 41623 12/1981 European Pat. Off. .
41624 12/1981 European Pat. Off. .
95104 11/1983 European Pat. Off. .

OTHER PUBLICATIONS

Cochran, J. L. et al, J. Org. Chem 26, pp. 808–811 (1961).
Oakes, V. et al, J. Chem. Soc. 1956, pp. 4433–4438.

Primary Examiner—Henry R. Jiles
Assistant Examiner—Dale A. Bjorkman
Attorney, Agent, or Firm—Edward McC. Roberts; Kevin T. Mansfield

[57] ABSTRACT

The invention relates to a process for the preparation of pyridine-2,3-dicarboxylic acid derivatives of formula

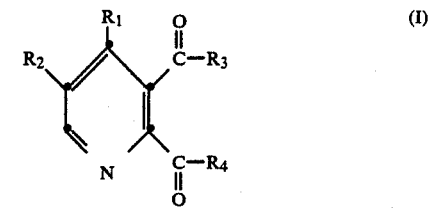

which process comprises reacting a hydrazone of formula II

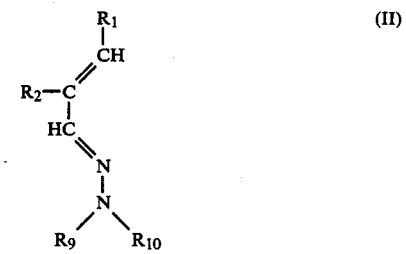

with a maleic acid derivative of formula III

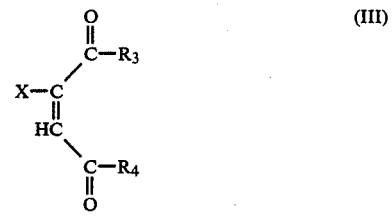

to give a 1-amino-1,4-dihydropyridine-2,3-dicarboxylic acid derivative of formula IV

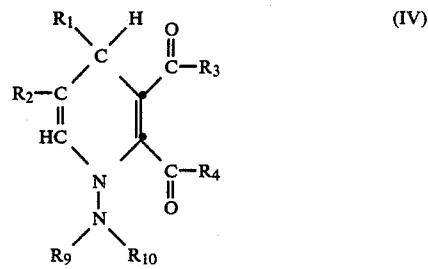

and subsequently removing $R_9R_{10}NH$. In the above formulae, $R_1$, $R_2$, $R_3$, $R_4$, $R_9$, $R_{10}$ and X are as defined in claim 1. The pyridine-2,3-dicarboxylic acid derivatives of formula I are intermediates for the preparation of herbicidal compounds.

14 Claims, No Drawings

PROCESS FOR THE PREPARATION OF PYRIDINE-2-3-DICARBOXYLIC ACID DERIVATIVES, AND NOVEL 1-AMINO-1,4-DIHYDROPYRIDINE-2-3-DIARBOXYLIC ACID DERIVATIVES

The present invention relates to a process for the preparation of pyridine-2,3-dicarboxylic acid derivatives, and to novel 1-amino-1,4-dihydropyridine-2,3-dicarboxylic acid derivatives which are obtained as intermediates when carrying out said process.

Herbicidal 2-(2-imidazolin-2-yl)pyridine-3-carboxylic acid derivatives which can be prepared from corresponding pyridine-2,3-dicarboxylic acids and derivatives thereof are known from European published application 0 041 623. However, so far no process has been available which makes it possible to prepare pyridine-2,3-dicarboxylic acids and derivatives thereof in simple manner from readily accessible starting materials. It is the object of the present invention to remedy this defect and to provide a process by which pyridine-2,3-dicarboxylic acids and derivatives thereof can be prepared in simple manner and in good yield from inexpensive and readily accessible starting materials.

Accordingly, the invention relates to a process for the preparation of pyridine-2,3-dicarboxylic acid derivatives of formula I

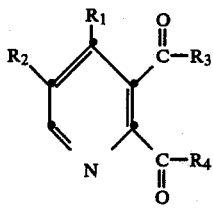

(I)

wherein $R_1$ is hydrogen, an unsubstituted or substituted, linear or branched alkyl, alkylthio or alkoxy group or an unsubstituted or substituted phenyl or phenoxy group, $R_2$ has the same meaning as $R_1$ and is additionally fluorine, chlorine or bromine, such as $R_3$ and $R_4$ independently of the other is —OH, —$NH_2$, —$NHR_5$, —$NR_5R_6$ or —$OR_7$, wherein $R_5$ and $R_6$ are alkyl, cycloalkyl, allyl, methallyl, propargyl, aryl or aralkyl, or $R_5$ and $R_6$ together are alkylene or oxaalkylene, and $R_7$ is alkyl, cycloalkyl, allyl, methallyl, propargyl, aralkyl or aryl, or $R_3$ and $R_4$ together are —O— or —$NR_8$—, wherein $R_8$ is hydrogen, unsubstituted or substituted, linear or branched alkyl, allyl, methallyl, propargyl, unsubstituted or substituted cycloalkyl, aryl or aralkyl, which process comprises reacting a hydrazone of formula II

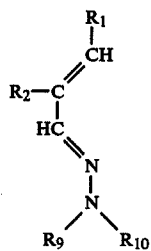

(II)

wherein each of $R_9$ and $R_{10}$ individually is alkyl, cycloalkyl, aralkyl or aryl, or $R_9$ and $R_{10}$ together are alkylene or oxaalkylene, with a maleic acid derivative of formula III

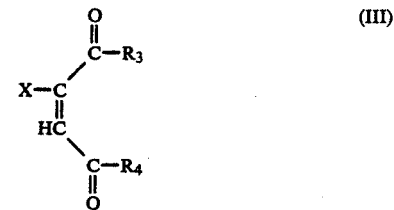

(III)

wherein $R_3$ and $R_4$ are as defined above and X is chlorine or bromine, in the presence of an inert solvent, to give a 1-amino-3,4-dihydropyridine-2,3-dicarboxylic acid derivative of formula IV

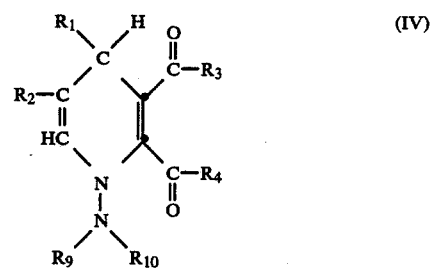

(IV)

wherein $R_1$, $R_2$, $R_3$, $R_4$, $R_9$ and $R_{10}$ are as defined above, and subsequently removing H-$NR_9R_{10}$ from said compound of formula IV by heating to give a pyridine-2,3-dicarboxylic acid derivative of formula I.

In the above formulae, $R_1$ and $R_2$ are alkyl, alkylthio and alkoxy preferably contain 1 to 6 carbon atoms. Suitable substituents of these radicals are hydroxy, halogen, preferably fluorine, chlorine and bromine, $C_1$-$C_4$alkoxy, phenyl, phenoxy, cyano, carboxyl and $C_1$-$C_4$alkoxycarbonyl. Preferred substituents are hydroxy and halogen. Examples of such radicals are: methyl, ethyl, n-propyl, isopropyl, n-butyl, isobutyl, tert-butyl, 1-pentyl, 3-pentyl, 1-hexyl, 2-hexyl, 3-hexyl, methoxy, ethoxy, n-propoxy, isopropoxy, n-butoxy, isobutoxy, tert-butoxy, methylthio, ethylthio, propylthio, butylthio, hydroxymethyl, 2-hydroxyethyl, fluoromethyl, trifluoromethyl, 2-cyanoethyl, 2-chloroethyl, bromoethyl, benzyl, chlorobenzyl, methoxymethyl, ethoxymethyl, methoxyethyl.

Suitable substituents of $R_1$ and $R_2$ are phenyl and phenoxy are e.g. halogen such as F, Cl and Br, CN, $C_1$-$C_4$alkyl, $C_1$-$C_4$alkoxy, $C_1$-$C_4$-haloalkyl or $C_1$-$C_4$-cyanoalkyl. Examples are methylphenyl, ethylphenyl, methoxyphenyl, ethoxypheny, chlorophenyl, fluorophenyl, difluorophenyl, bromophenyl, chlorophenoxy, methylphenoxy, methoxyphenoxy, fluoromethylphenyl, difluoromethylphenyl, trifluoromethylphenyl, chloromethylphenyl, cyanomethylphenyl, 2-cyanoethylphenyl, trifluoromethylphenoxy and cyanomethylphenoxy.

$R_3$ and $R_4$ are preferably —OH or $OR_7$, and $OR_3$ and $R_4$ together are preferably —O— or —$NR_8$—. $R_5$ and $R_6$ are alkyl preferably contain 1 to 6, most preferably 1 to 4, carbon atoms. $R_5$ and $R_6$ are cycloalkyl are preferably cyclopentyl or cyclohexyl. Where $R_5$ and $R_6$ together are alkylene, they are preferably pentamethylene or tetramethylene, and where $R_5$ and $R_6$ together are oxaalkylene, they are preferably 3-oxapentylene, $R_5$ and $R_6$ are aryl or aralkyl are preferably $C_6$-$C_{16}$aryl or $C_7$–$C_{16}$aralkyl respectively, with the most preferred meanings being phenyl or benzyl which may be substituted in the same manner as phenyl represented by $R_1$ to $R_3$.

$R_7$ are alkyl may be linear or branched and preferably contains 1 to 6 carbon atoms. $R_7$ are cycloalkyl is preferably cyclopentyl or cyclohexyl. $R_7$ as aryl or aralkyl is preferably phenyl or benzyl which may be substituted e.g. by $C_1$–$C_4$alkyl, $C_1$–$C_4$-alkoxy or halogen such as fluorine, chlorine or bromine.

Suitable substituents of $R_8$ are e.g. —OH, —OR$_{11}$, —SR$_{11}$, wherein $R_{11}$ is $C_1$–$C_6$alkyl, cyclohexyl or phenyl, or are —NR$_9$R$_{10}$, —COOH, —COOR$_7$, —O-COR$_{11}$, —CONH$_2$, —CONHR$_5$, —CONR$_5$R$_6$ and halogen such as fluorine, chlorine or bromine, and cyano. $R_8$ as alkyl preferably contains 1 to 6 carbon atoms. Examples have been given above.

$R_8$ as cycloalkyl is preferably cyclohexyl or cyclopentyl. Examples of $R_8$ as substituted radicals are hydroxymethyl, 2-hydroxyethyl, methoxymethyl, methoxyethyl, ethoxyethyl, phenoxyethyl, dimethylamino, diethylamino, methoxycarbonylmethyl, ethoxycarbonylethyl, propoxycarbonylmethyl, phenoxycarbonylmethyl, benzoyloxymethyl, acetoyloxyethyl, methylaminocarbonylmethyl, dimethylaminocarbonylethyl, chloromethyl, 2-chloroethyl, cyanomethyl, 2-cyanoethyl, 2-cyanopropyl, 2-[2-cyano-3-methyl]butyl and 2-[2-carbamoyl-3-methyl]butyl.

$R_9$ and $R_{10}$ as alkyl may be linear or branched and preferably contain 1 to 6, most preferably 1 to 4, carbon atoms. Particularly preferred radicals $R_9$ and $R_{10}$ are ethyl or methyl. $R_9$ and $R_{10}$ are cyloalkyl are preferably cyclopentyl or cyclohexyl, and as aryl they are preferably phenyl and as aralkyl preferably phenylalkyl, most preferably benzyl. In a preferred embodiment, $R_9$ is phenyl and $R_{10}$ is $C_1$–$C_6$alkyl. Where $R_9$ and $R_{10}$ together are alkylene, they are preferably tetramethylene or pentamethylene, and where $R_9$ and $R_{10}$ together are oxaalkylene, they are preferably 3-oxapentylene.

In a preferred embodiment, $R_3$ and $R_4$ are a radical of the formula

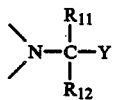

wherein Y is —CN or —CONH$_2$ and each of $R_{11}$ and $R_{12}$ independently of the other is a hydrogen atom or linear or branched $C_1$–$C_6$alkyl. $R_{11}$ and $R_{12}$ are preferably linear or branched $C_1$–$C_4$alkyl.

In a particularly preferred subgroup, $R_3$ and $R_4$ are —O—, >N—phenyl, >N—$C_1$–$C_4$alkyl,

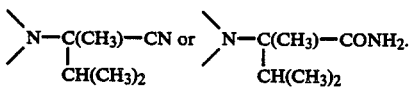

Suitable solvents for carrying out the process of the present invention are e.g. polar, aprotic solvents which may be used alone or in mixtures comprising at least 2 solvents. Examples of such solvents are: ethers such as dibutyl ether, tetrahydrofuran, dioxan, methylene glycol, dimethylethylene glycol, diethyldiethylene glycol, dimethyltriethylene glycol, halogenated hydrocarbons such as methylene chloride, chloroform, 1,2-dichloroethane, 1,1,1-trichloroethane, 1,1,2,2-tetrachloroethane, carboxylates and lactones such as ethyl acetate, methyl propionate, ethyl benzoate, 2-methoxyethyl acetate, γ-butyrolactone, σ-valerolactone and pivalolactone, carboxamides and lactams such as formamide, acetamide, N-methylformamide, N,N-dimethylformamide, N,N-diethylformamide, N,N-dimethylacetamide, N,N-diethylacetamide, γ-butyrolactam, ξ-caprolactam, N-methylpyrrolidone, N-acetylpyrrolidone, N-methylcaprolactam, tetramethylurea, hexamethylphosphoric triamide, sulfoxides such as dimethylsulfoxide, sulfones such as dimethyl sulfone, diethyl sulfone, trimethylene sulfone, tetramethylene sulfone, trimethylamine, triethylamine, N-methylpyrrolidine, N-methylpiperidine, N-methylmorpholine, substituted benzenes such as chlorobenzene, nitrobenzene, nitriles such as acetonitrile.

The compounds of formulae II and III are known or they can be prepared by known methods. They are preferably employed in equimolar amounts. A small excess of the unsaturated hydrazones of formula I can also be used.

The reaction is preferably carried out in the temperature range from 0° C. to 200° C., most preferably from 0° C. to 150° C. If the temperature is at least 20° C., preferably at least 40° C., the compounds of formula I are obtained direct. By isomerising the starting materials of formula II, mixtures of position isomers of formula I can be formed.

In a preferred embodiment of the process of the present invention, it is convenient to carry out the reaction of a hydrazone of formula II with a maleic acid derivative of formula III to give a 1-amino-1,4-dihydropyridine-2,3-dicarboxylic acid derivative of formula IV in the presence of a base and subsequently to remove $R_9R_{10}NH$ from the compound of formula IV by treatment with an acid or by heat treatment at a temperature of at least 20° C. in a neutral medium to give a compound of formula I. $R_1$ to $R_4$ and $R_9$ and $R_{10}$ are as defined for formulae I and II, including the preferences.

In the first step, the reaction temperature is preferably in the range from 0° C. to 100° C., most preferably from 0° C. to 50° C. Suitable bases are e.g. alkali metal carbonates such as lithium, sodium or potassium carbonate, and in particular, organic amines, most particularly tertiary amines which may simultaneously act as solvents. Preferred tertiary amines are those containing $C_1$–$C_4$alkyl radicals, e.g. triethylamine.

The 1-amino-1,4-dihydropyridine-2,3-dicarboxylic acid derivatives of formula IV may be isolated before the second reaction step. The heat treatment is preferably effected in the temperature range from 20° C. to 150° C., most preferably from 40° C. to 100° C. Suitable mineral acids are e.g. hydrochloric acid, hydrobromic acid, hydriodic acid, perchloric acid or sulfuric acid. If $R_3$ and $R_4$ are groups which are susceptible to hydrolysis, it is preferred to use a solution of hydrogen chloride, hydrogen bromide or hydrogen iodide in an organic solvent.

To prepare compounds of formula I, it is also possible to convert acids or acid derivatives of formula I into other compounds of formula I by known methods, e.g. the anhydrides into amides, imides, hemiesters, diesters, amidates or amidic acids.

The process of the present invention is particularly suitable for the preparation of pyridine-2,3-dicarboxylic acid derivatives of formula I, wherein $R_1$ is hydrogen or methyl, $R_2$ is hydrogen, $C_1$–$C_6$alkyl, fluorine, chlorine, bromine, $C_1$-$C_6$alkoxy, $C_1$-$C_4$alkylthio, phenoxy, $C_1$-$C_6$hydroxyalkyl, $C_1$-$C_6$haloalkyl, or phenyl which is unsubstituted or substituted by $C_1$-$C_4$alkyl, $C_1$-$C_4$alkoxy or halogen, and each of $R_3$ and $R_4$ individually is —OH or —OR$_7$, and $R_3$ and $R_4$ together are —O— or —NR$_8$—. The process of this invention is most particularly suitable for the preparation of pyridine-2,3-dicarboxylic acid derivatives of formula I, wherein $R_1$ is hydrogen, $R_2$ is $C_1$-$C_6$alkyl and each of $R_3$ and $R_4$ individually is —OH or —OR$_7$, or $R_3$ and $R_4$ together are a group of the formula

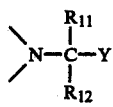

in which formulae each of $R_8$, $R_{11}$ and $R_{12}$ is as defined above and Y is a cyano or a carbamoyl group.

The 1-amino-1,4-dihydropyridine-2,3-dicarboxylic acid derivatives of formula IV which are obtained by reacting a hydrazone of formula II with a maleic acid derivative of formula III in the presence of a base are novel compounds and likewise constitute an object of the present invention. In compounds of formula IV, $R_1$ and $R_2$ are preferably a hydrogen atom, $C_1$-$C_6$alkyl, $C_1$-$C_6$alkylthio, $C_1$-$C_6$alkoxy, $C_1$-$C_6$hydroxyalkyl, $C_2$-$C_6$alkoxyalkyl, $C_1$-$C_6$haloalkyl, phenyl, phenoxy, or phenyl or phenoxy substituted by $C_1$-$C_4$alkyl, $C_1$-$C_4$alkoxy or halogen, $R_3$ and $R_4$ are preferably —OH, —NH$_2$, —NHR$_5$, —NR$_5$R$_6$ or —OR$_7$, wherein $R_5$ and $R_6$ are $C_1$-$C_6$alkyl, cyclopentyl, cyclohexyl, phenyl or benzyl, or $R_5$ and $R_6$ together are trimethylene, tetramethylene or 3-oxapentylene, or $R_3$ and $R_4$ together are —O— or —NR$_8$, wherein $R_8$ is $C_1$-$C_6$alkyl, $C_1$-$C_6$cyanoalkyl, $C_1$-$C_6$aminocarbonylalkyl or phenyl. $R_9$ and $R_{10}$ are preferably $C_1$-$C_6$alkyl or phenyl, or $R_9$ and $R_{10}$ together are preferably pentamethylene, tetramethylene or 3-oxapentylene.

Preferred compounds of formula IV are those wherein $R_1$ is hydrogen, $R_2$ is ethyl, n-propyl, isopropyl or n-butyl, $R_9$ and $R_{10}$ are methyl and $R_3$ and $R_4$ together are a group of the formula

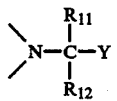

wherein $R_{11}$ is methyl, $R_{12}$ is isopropyl and Y is cyano or carbamoyl.

The novel compounds of formula Ia

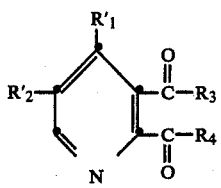

wherein $R'_1$ is hydrogen or methyl, $R'_2$ is $C_1$-$C_6$alkyl or fluorine, with the proviso that, if $R'_1$ is methyl, $R'_2$ may also be chlorine or bromine, and $R_3$ and $R_4$ are as defined for formula I, constitute a further object of the invention. Preferred compounds of formula Ia are those wherein $R'_1$ is hydrogen, $R'_2$ is $C_1$-$C_4$alkyl and each of $R_3$ and $R_4$ individually is —OH or O—$C_1$-$C_4$alkyl, and $R_3$ and $R_4$ together are —O—, —NR$_8$ and, in particular, a group of the formula

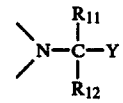

in which formulae $R_8$, $R_{11}$, $R_{12}$ and Y are as defined above.

Pure pyridine-2,3-dicarboxylic acid derivatives of formula I are obtained in high yield by the process of the present invention using readily accessible starting materials by a short synthesis route and under mild reaction conditions. The process is particularly suitable for industrial application.

The compounds of formula I are valuable intermediates, in particular for the preparation of herbicides as described e.g. in European published applications 0 041 623, 0 041 624 and 0 095 104.

The following Examples illustrate the invention in more detail.

EXAMPLE 1

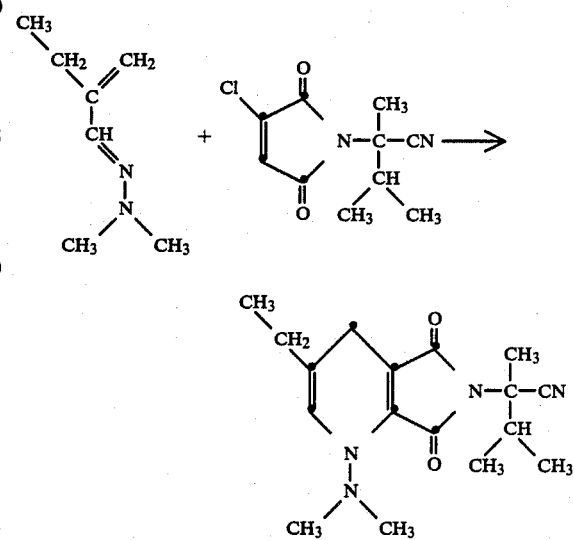

A reaction vessel is charged with 22.8 (0.1 mol) of chlorinated imide in 100 ml of acetonitrile and 28 ml (0.2 mol) of triethylamine are added to the reaction mixture. 13.9 g (0.11 mol) of the hydrazone are added dropwise at room temperature. After the exothermic reaction has subsided, the reaction mixture is stirred for ½ hour at 50° C. The mixture is then filtered and the filter is concentrated by evaporation. The residue is chromatographed over silica gel eluted with toluene/ethyl acetate (16:1), affording 22.5 g of the dihydropyridine in the form of a red oil which crystallises on standing. Melting point: 50°–51° C.

The following dihydropyridines are obtained in analogous manner:

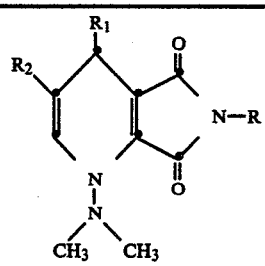
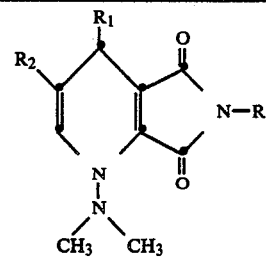

| R | R₁ | R₂ | m.p. |
|---|---|---|---|
| C₆H₅ | H | C₂H₅ | 70–72° |
| C₆H₅ | CH₃ | CH₃ | oil |
| C₆H₅ | H | n-C₃H₇ | 96° |
| C₆H₅ | C₂H₅ | CH₃ | oil |
| C₆H₅ | H | i-C₃H₇ | 94–95° |
| C₆H₅ | CH₃ | H | 100° |
| C₆H₅ | C₆H₅ | H | 130–132° |
| C₆H₅ | C₆H₅ | CH₃ | 163–165° |
| -C(CH₃)(CO-NH₂)-CH(CH₃)(CH₃) | H | C₂H₅ | 97–99° |
| -C(CH₃)(CO-NH₂)-CH(CH₃)(CH₃) | H | CH₃ | |
| -C(CH₃)(CO-NH₂)-CH(CH₃)(CH₃) | H | C₄H₉ | |
| -C(CH₃)(CO-NH₂)-CH(CH₃)(CH₃) | H | CH₂-CH₂-Cl | |
| -C(CH₃)(CO-NH₂)-CH(CH₃)(CH₃) | H | CH₂OCH₃ | |
| -C(CH₃)(CO-NH₂)-CH(CH₃)(CH₃) | H | CF₃ | |
| -C(CH₃)(CN)-CH(CH₃)(CH₃) | H | CH₃ | |
| -C(CH₃)(CN)-CH(CH₃)(CH₃) | H | C₄H₉ | |
| -C(CH₃)(CN)-CH(CH₃)(CH₃) | H | -O-CH₃ | |
| -C(CH₃)(CN)-CH(CH₃)(CH₃) | H | SCH₃ | |
| -C(CH₃)(CN)-CH(CH₃)(CH₃) | H | -N(CH₃)(CH₃) | |
| -C(CH₃)(CN)-CH(CH₃)(CH₃) | H | Cl | |
| -C(CH₃)(CN)-CH(CH₃)(CH₃) | H | SCH₃ | |

EXAMPLE 2

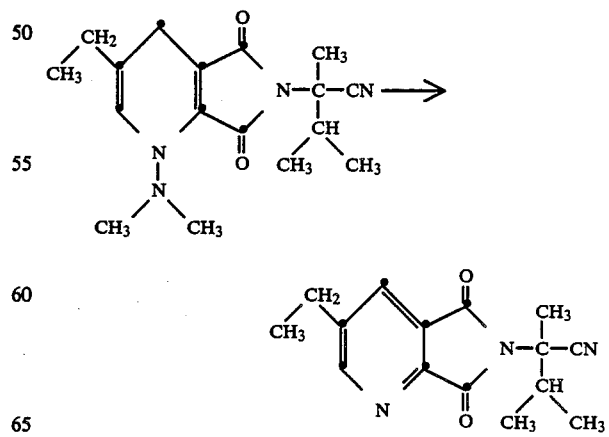

A reaction vessel is charged with 22 g of dihydropyridine in 100 ml of dioxan. A solution of 100 ml of dioxan containing 10% gaseous HCl is added dropwise at 8° C. The reaction mixture is then heated to room temperature and stirred for 2 hours. The mixture is then cautiously neutralised with a solution of sodium carbonate, then diluted with chloroform, washed with water, dried over MgSO$_4$ and concentrated by evaporation. The residue is chromatographed over silica gel as in Example 1, affording the pyridine as a beige powder. Melting point: 72°–73° C.

Concentrated HCl may be used in place of gaseous HCl.

The following compounds are obtained in analogous manner:

| R | R$_1$ | R$_2$ | m.p. |
|---|---|---|---|
| C$_6$H$_5$ | H | C$_2$H$_5$ | 190–191° |
| C$_6$H$_5$ | CH$_3$ | CH$_3$ | 165–166° |
| C$_6$H$_5$ | H | n-C$_3$H$_7$ | 149–151° |
| C$_6$H$_5$ | C$_2$H$_5$ | CH$_3$ | 174–176° |
| C$_6$H$_5$ | n-C$_3$H$_7$ | C$_2$H$_5$ | 94–96° |
| C$_6$H$_5$ | CH$_3$ | n-C$_4$H$_9$ | 149–151° |
| C$_6$H$_5$ | H | n-C$_4$H$_9$ | 108–110° |
| C$_6$H$_5$ | n-C$_3$H$_7$ | CH$_3$ | 122–124° |
| C$_6$H$_5$ | H | i-C$_3$H$_7$ | 124–126° |
| C$_6$H$_5$ | H | CH$_3$ | 244–246° |
| C$_6$H$_5$ | C$_6$H$_5$ | H | 202–203° |
| C$_6$H$_5$ | p-NMe$_2$—C$_6$H$_4$ | H | 206–208° |
| C$_6$H$_5$ | H | (CH$_2$)$_2$CN | 190–191° |
| C$_6$H$_5$ | CH$_3$ | n-C$_4$H$_9$ | 149–151° |
| C$_6$H$_5$ | CH$_3$ | H | |
| C$_6$H$_5$ | n-C$_3$H$_7$ | H | |
| —C(CH$_3$)(CO—NH$_2$)—CH(CH$_3$)$_2$ | H | Cl | |
| —C(CH$_3$)(CO—NH$_2$)—CH(CH$_3$)$_2$ | H | OCH$_3$ | |
| —C(CH$_3$)(CO—NH$_2$)—CH(CH$_3$)$_2$ | H | S—CH$_3$ | |
| —C(CH$_3$)(CO—NH$_2$)—CH(CH$_3$)$_2$ | H | CH$_2$—N(CH$_3$)$_2$ | |
| —C(CH$_3$)(CO—NH$_2$)—CH(CH$_3$)$_2$ | H | CH$_2$—CH$_2$—Cl | |
| —C(CH$_3$)(CO—NH$_2$)—CH(CH$_3$)$_2$ | H | CH$_2$—O—CH$_3$ | |

-continued
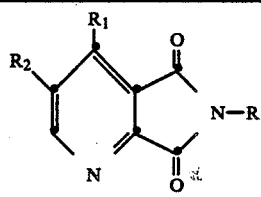
| R | $R_1$ | $R_2$ | m.p. |
|---|---|---|---|
| CH₃-C(CH(CH₃)₂)(CO-NH₂)- with CH₃ | H | SO₂CH₃ | |
| CH₃-C(CH(CH₃)₂)(CO-NH₂)- with CH₃ | CH₃ | F | 178° (decomp.) |
| C₆H₅ | n-C₃H₅ | CH₃ | 177–179° |
| C₆H₅ | H | C₄H₉(t) | |
| C₆H₅ | H | CH₂—CH₂Br | |
| C₆H₅ | C₆H₅ | C₂H₅ | — |
| C₆H₅ | CH₃ | CH₂COOCH₃ | 119–120° |
| C₆H₅ | H | C₄H₉(s) | |
| C₆H₅ | H | CH₃ | 244–246° |
| CH₃-C(CH(CH₃)₂)(CN)- | H | n-C₃H₇ | 59–60° |
| CH₃-C(CH(CH₃)₂)(CN)- | C₂H₅ | CH₃ | 105–107° |
| CH₃-C(CH(CH₃)₂)(CN)- | n-C₃H₇ | C₂H₅ | 76–70° |
| CH₃-C(CH(CH₃)₂)(CN)- | CH₃ | CH₂—CH₂Br | |
| CH₃-C(CH(CH₃)₂)(CN)- | C₆H₅ | CH₃ | |
| CH₃-C(CH(CH₃)₂)(CN)- | C₆H₅ | C₂H₅ | 142–143° |

-continued
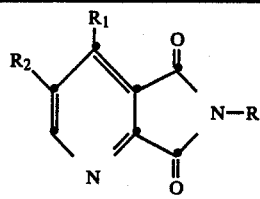
| R | $R_1$ | $R_2$ | m.p. |
|---|---|---|---|
| -C(CH₃)(CN)-CH(CH₃)(CH₃) | CH₃ | CH₂COOCH₃ | oil |
| -C(CH₃)(CN)-CH(CH₃)(CH₃) | H | n-C₄H₉ | oil |
| -C(CH₃)(CN)-CH(CH₃)(CH₃) | H | i-C₃H₇ | 95–96° |
| -C(CH₃)(CN)-CH(CH₃)(CH₃) | 4-Cl | CH₃ | 112–114° |
| -C(CH₃)(CN)-CH(CH₃)(CH₃) | 3-NO₂—C₆H₄ | CH₃ | 164–166° |
| -C(CH₃)(CN)-CH(CH₃)(CH₃) | H | CH₃ | 119–120° |
| 2-F,3-Cl,5-(O-CH(CH₃)₂)-C₆H₂ | C₂H₅ | CH₃ | 67–69° |
| -C(CH₃)(CN)-CH(CH₃)(CH₃) | H | CH₂—COOC₂H₅ | |
| -C(CH₃)(CN)-CH(CH₃)(CH₃) | CH₃ | F | oil |

-continued

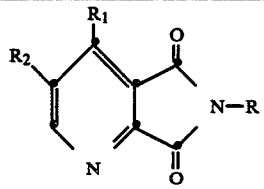

| R | R1 | R2 | m.p. |
|---|----|----|------|
| -C(CH3)(CN)-CH(CH3)(CH3) | H | CH2-C6H5 | |
| -C(CH3)(CN)-CH(CH3)(CH3) | H | OCH3 | |
| -C(CH3)(CN)-CH(CH3)(CH3) | H | Cl | |
| -C(CH3)(CN)-CH(CH3)(CH3) | H | SCH3 | |
| -C(CH3)(CN)-CH(CH3)(CH3) | H | CH2—O—CH3 | |
| -C(CH3)(CN)-CH(CH3)(CH3) | H | CH2—O—CO—CH3 | |

EXAMPLE 3

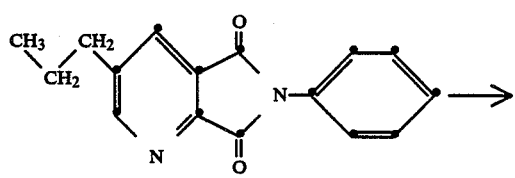

5.0 of imide together with 75 ml of concentrated HCl are heated under reflux. After 3½ hours the reaction mixture is concentrated by evaporation, the residue is taken up in water and this solution is in turn concentrated by evaporation. The pyridine-2,3-dicarboxylic acid is recrystallised from ethanol. Melting point: 160°–163° C. (decomp.).

The following compounds are obtained in analogous manner:

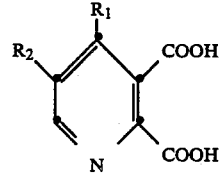

| R1 | R2 | m.p. |
|----|----|------|
| H | i-C3H7 | 147–148° |
| H | F | |
| H | Cl | |
| CH3 | CH3 | |
| CH3 | OCH3 | |

-continued

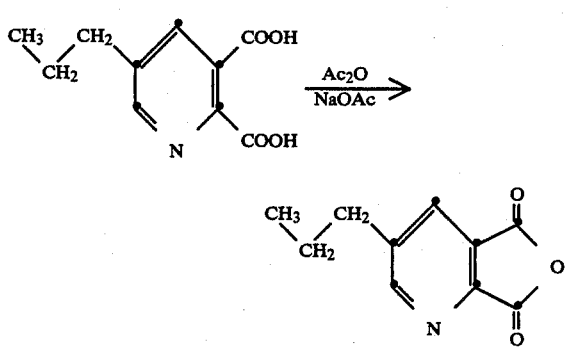

| R₁ | R₂ | m.p. |
|---|---|---|
| F | H | |
| Cl | H | |
| Cl | CH₃ | |
| C₂H₅ | CH₃ | |
| C₄H₉ | H | |
| H | C₄H₉(i) | |
| H | C₂H₅ | |
| H | C₃H₇ | |
| H | C₄H₉(+) | |
| H | OCH₃ | |
| H | CH₃ | |
| H | CH₂—CH₂—Cl | |
| H | CH₂—CH₂—CN | |
| H | SO₂CH₃ | |
| H | CH₂—O—CH₃ | |
| H | CH₂—OH | |
| H | CH₂—⌬ | |
| H | O—⌬ | |

EXAMPLE 4:

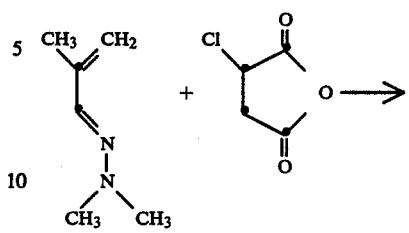

2 g of 5-propylpyridine-2,3-dicarboxylic acid together with 25 ml of acetic anhydride and 2 g of anhydrous sodium acetate are heated for 1 hour at 70° C. After removal of the acetic anhydride by evaporation, the residue is partitioned between water and chloroform and the organic phase is dried over MgSO₄ and then concentrated by evaporation. The residue is crystallised from ether/hexane, affording 5-propylpyridine-2,3-dicarboxylic anhydride with a melting point of 42°–44° C.

In analogous manner, 5-isopropylpyridine-2,3-dicarboxylic anhydride with a melting point of 66°–67° C. is obtained from 5-isopropylpyridine-2,3-dicarboxylic acid and 5-ethylpyridine-2,3-dicarboxylic anhydride with a melting point of 71°–72° C. is obtained from 5-ethylpyridine-2,3-dicarboxylic acid.

EXAMPLE 5

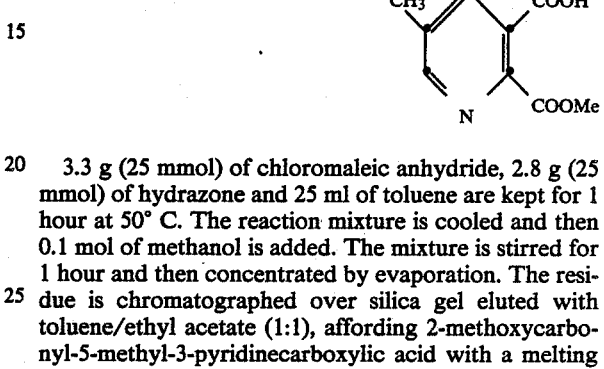

3.3 g (25 mmol) of chloromaleic anhydride, 2.8 g (25 mmol) of hydrazone and 25 ml of toluene are kept for 1 hour at 50° C. The reaction mixture is cooled and then 0.1 mol of methanol is added. The mixture is stirred for 1 hour and then concentrated by evaporation. The residue is chromatographed over silica gel eluted with toluene/ethyl acetate (1:1), affording 2-methoxycarbonyl-5-methyl-3-pyridinecarboxylic acid with a melting point of 200° C. in the form of white crystals.

EXAMPLE 6

The procedure of Example 5 is repeated using the corresponding 4-methylhydrazone to give 4-methyl-2-methoxycarbonyl-3-pyridinecarboxylic acid with a melting point of 200° C. (decomp.).

EXAMPLE 7

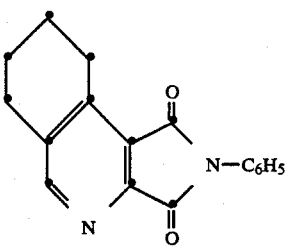

7.6 g (0.05 mol) of hydrazone and 10.4 g (0.05 mol) of imide together with 14 ml (0.1 mol) of triethylamine in 80 ml of CH₃CN are heated for 7½ hours to 70° C. The reaction mixture is cooled, then concentrated by evaporation and the residue is suspended in 20 ml of dioxan. A 10% solution of gaseous HCl in dioxan (circa 30 ml) is added dropwise at 10°–20° C. for the suspension, the batch is stirred for 2½ hours and then concentrated by evaporation. The residue is dissolved in chloroform and the solution is washed with 2N sodium carbonate, dried and concentrated by evaporation. The residue is chromatographed over silica gel eluted with toluene/ethyl acetate, affording 6.0 g of beige powder with a melting point of 142°–145° C.

The following compounds are obtained in analogous manner:

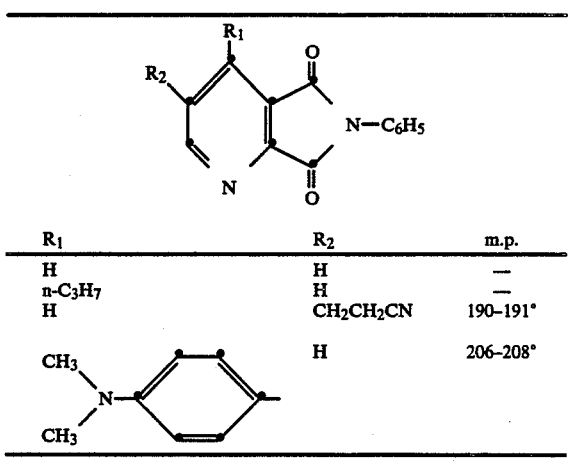

| $R_1$ | $R_2$ | m.p. |
|---|---|---|
| H | H | — |
| n-$C_3H_7$ | H | — |
| H | $CH_2CH_2CN$ | 190–191° |
| $CH_3\text{-N-}CH_3$ (with phenyl) | H | 206–208° |

EXAMPLE 8:

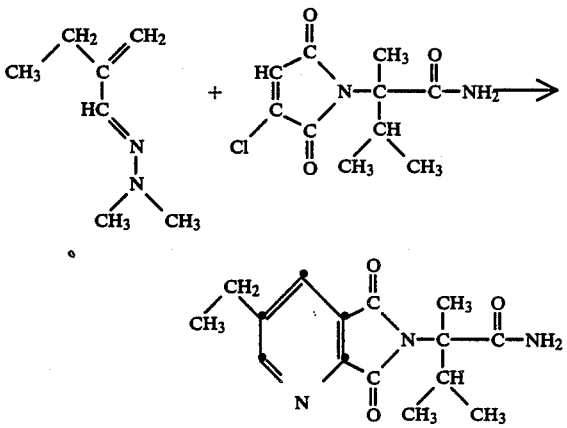

63 g of hydrazone and 122 g of chloromaleic imide are introduced into a solution of 101 g of triethylamine in 1000 ml of acetonitrile. The reaction mixture is heated for 8 hours to 70° C., then cooled to room temperature and filtered. The filtrate is concentrated by evaporation in vacuo. The residue is dissolved in dioxan and a 10% solution of hydrogen chloride in dioxan is added dropwise at 10°–20° C. When the addition is complete, the mixture is stirred for 1½ hours at room temperature, then diluted with chloroform and cautiously neutralised with a solution of 2N sodium carbonate. The organic phase is then separated, washed with water, dried over magnesium sulfate and concentrated by evaporation. The residue is crystallised from ether/hexane, affording 105 g of 3-ethyl-5,7-dihydro-α-isopropyl-α-methyl-5,7-dioxo-6H-pyrrolo[3,4-b]pyridine-6-acetamide with a melting point of 115°–117° C.

EXAMPLE 9

54.2 g of 3-ethyl-5,7-dihydro-α-isopropyl-α-methyl-5,7-dioxo-6H-pyrrolo[3,4-b]pyridine-6-acetonitrile are stirred in portions over 30 minutes into 60 ml of concentrated sulfuric acid (96%). To complete the reaction, the mixture is heated for 2 hours to 65° C.

For working up, circa 150 g of ice diluted with 500 ml of ice water are added and the solution is buffered by addition of 75 g of sodium acetate. After stirring for 2 hours at 0° C., crystallisation is complete and the product is isolated by filtration. For purification, the residue is taken up in 400 ml of methylene chloride, the solution is washed with water, dried over sodium sulfate and then substantially concentrated by rotary evaporation. The residue is crystallised from petroleum ether.

56.4 g of 3-ethyl-5,7-dihydro-α-isopropyl-α-methyl-5,7-dioxa-6H-pyrrolo[3,4-b]pyridine-6-acetamide with a melting point of 114°–117° C. are obtained.

What is claimed is:

1. A process for the preparation of a pyridine-2,3-dicarboxylic acid derivative of formula I

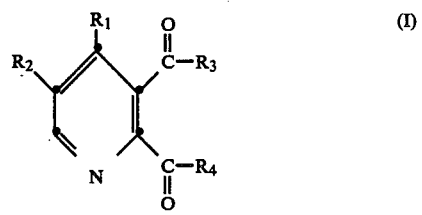

wherein $R_1$ is hydrogen or $C_1$–$C_6$alkyl, $C_1$–$C_6$alkylthio or $C_1$–$C_6$alkoxy which are unsubstituted or substituted by hydroxy, halogen, $C_1$–$C_4$alkoxy, phenyl, phenoxy, cyano, carboxyl or $C_1$–$C_4$alkoxycarbonyl; or phenyl or phenoxy, unsubstituted or substituted by halogen, cyano, $C_1$–$C_4$alkyl, $C_1$–$C_4$alkoxy, $C_1$–$C_4$haloalkyl or $C_1$–$C_4$cyanoalkyl, $R_2$ has the meaning as $R_1$ and is additionally fluorine, chlorine or bromine, each of $R_3$ and $R_4$ independently of the other is —OH, —$NH_2$, —$NHR_5$, —$NR_5R_6$ or —$OR_7$, wherein $R_5$ and $R_6$ are $C_1$–$C_6$alkyl, $C_5$–$C_6$cycloalkyl, allyl, methallyl, propargyl, unsubstituted $C_6$–$C_{16}$aryl or $C_7$–$C_{16}$aralkyl or $C_6$–$C_{16}$aryl or $C_7$–$C_{16}$aralkyl which are substituted by halogen, cyano, $C_1$–$C_4$alkyl, $C_1$–$C_4$alkoxy, $C_1$–$C_4$haloalkyl or $C_1$–$C_4$cyanoalkyl, or $R_5$ and $R_6$ together are $C_4$–$C_5$alkylene or 3-oxapentalene, and $R_7$ is unsubstituted $C_1$–$C_6$alkyl or $C_1$–$C_6$alkyl substituted by —OH, —$OR_{11}$ or —$SR_{11}$, —$NR_9R_{10}$, —COOH, —$COOR_7$, —$OCOR_{11}$, —$CONH_2$, —$CONHR_5$, —$CONR_5R_6$, halogen or cyano; or is $C_5$–$C_6$cycloalkyl, allyl, methallyl, propargyl unsubstituted phenyl or benzyl or phenyl or benzyl which is substituted by $C_1$–$C_4$alkyl, $C_1$–$C_4$alkoxy or halogen, wherein each of $R_9$ and $R_{10}$ individually is $C_1$–$C_6$alkyl, $C_5$–$C_6$cycloalkyl, phenyl or benzyl, or $R_9$ and $R_{10}$ together are $C_4$–$C_5$alkylene or 3-oxypentalene and $R_{11}$ is $C_1$–$C_6$alkyl, cyclohexyl or phenyl; or $R_3$ and $R_4$ taken together are —O— or —$NR_8$— wherein $R_8$ is hydrogen or $R_7$, which process comprises reacting a hydrazone of formula II

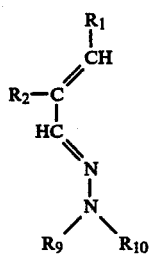

(II)

wherein $R_1$, $R_2$, $R_9$ and $R_{10}$ are as previously defined, with a maleic acid derivative of formula III

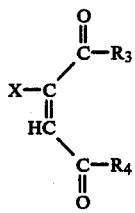

(III)

wherein $R_3$ and $R_4$ are as previously defined and X is chlorine or bromine, in the presence of an inert solvent, to give a 1-amino-3,4-dihydropyridine-2,3-dicarboxylic acid derivative of formula IV

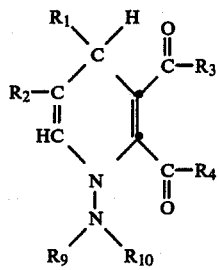

(IV)

wherein $R_1$, $R_2$, $R_3$, $R_4$, $R_9$ and $R_{10}$ are as defined above, and subsequently removing H—$NR_9R_{10}$ from said compound of formula IV by treatment with an acid or by heat treatment at a temperature of at least 20° C. in neutral medium to give a pyridine-2,3-dicarboxylic acid derivative of formula I.

2. A process according to claim 1, which comprises carrying out the reaction of the hydrazone of formula II with the maleic acid derivative of formula III at a temperature in the range from 0° C. to 200° C.

3. A process according to claim 1, which comprises carrying out the reaction of the hydrazone of formula II with the maleic acid derivative of formula III at a temperature in the range from 0° C. to 150° C.

4. A process according to claim 1, which comprises using a hydrazone of formula II, wherein $R_9$ and $R_{10}$ are $C_1$-$C_4$alkyl.

5. A process according to claim 1, which comprises carrying out the reaction of a hydrazone of formula II with a maleic acid derivative of formula III at a temperature in the range from 0° to 150° C. and in the presence of a tertiary amine.

6. A process according to claim 1, which comprises carrying out the conversion of a 1-amino-3,4-dihydropyridine-2,3-dicarboxylic acid derivative of formula IV into a pyridine-2,3-dicarboxylic acid derivative of formula I by treatment with a mineral acid and at a temperature in the range from 20° C. to 150° C.

7. A process according to claim 1, which comprises carrying out the conversion of a 1-amino-3,4-dihydropyridine-2,3-dicarboxylic acid derivative of formula IV into a pyridine-2,3-dicarboxylic acid derivative of formula I by heat treatment in a neutral reaction medium and at a temperature in the range from 40° C. to 100° C.

8. A process according to claim 1, which process comprises carrying out the reaction in the presence of a polar aprotic solvent.

9. A process according to claim 1, which comprises using a maleic acid derivative of formula III, wherein $R_3$ and $R_4$ together are a radical of the formula

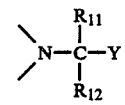

wherein Y is —CN or —$CONH_2$ and each of $R_{11}$ and $R_{12}$ independently of the other is hydrogen or $C_1$-$C_6$alkyl.

10. A process according to claim 1, which comprises preparing a pyridine-2,3-dicarboxylic acid derivative of formula I, wherein $R_1$ is hydrogen or methyl, $R_2$ is hydrogen, $C_1$-$C_6$alkyl, fluorine, chlorine, bromine, $C_1$-$C_6$alkoxy, $C_1$-$C_4$alkylthio, phenoxy, $C_1$-$C_6$hydroxyalkyl, $C_1$-$C_6$haloalkyl, or phenyl which is unsubstituted or substituted by $C_1$-$C_4$alkyl, $C_1$-$C_4$alkoxy or halogen, and each of $R_3$ and $R_4$ individually is —OH or —$OR_7$, or $R_3$ and $R_4$ together are —O— or —$NR_8$—.

11. A process according to claim 1, which comprises preparing a pyridine-2,3-dicarboxylic acid derivative of formula I, wherein $R_1$ is hydrogen, $R_2$ is $C_1$-$C_6$alkyl and each of $R_3$ and $R_4$ individually is —OH or —OR, or $R_3$ and $R_4$ together are a group of the formula

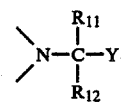

in which formulae each of $R_8$, $R_{11}$ and $R_{12}$ is as defined above and Y is a cyano or carbamoyl group.

12. A 1-amino-1,4-dihydropyridine-2,3-dicarboxylic acid derivative of formula IV

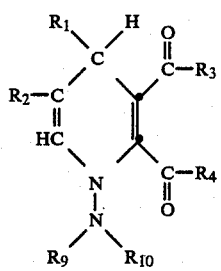

(IV)

wherein
$R_1$ is hydrogen or $C_1$-$C_6$alkyl, $C_1$-$C_6$alkylthio or $C_1$-$C_6$alkoxy which are unsubstituted or substituted by hydroxy, halogen, $C_1$-$C_4$alkoxy, phenyl, phenoxy, cyano, carboxyl or $C_1$-$C_4$alkoxycarbonyl; or phenyl or phenoxy, unsubstituted or substituted by halogen, cyano, $C_1$–$C_4$alkyl, $C_1$–$C_4$alkoxy, $C_1$–$C_4$haloalkyl or $C_1$–$C_4$cyanoalkyl, $R_2$ has the meaning as $R_1$ and is additionally fluorine, chlorine or bromine, each of $R_3$ and $R_4$ independently of the other is —OH, —$NH_2$, —$NHR_5$, —$NR_5R_6$ or —$OR_7$, wherein $R_5$ and $R_6$ are $C_1$–$C_6$alkyl, $C_5$–$C_6$cycloalkyl, allyl, methallyl, propargyl, unsubstituted $C_6$–$C_{16}$aryl or $C_7$–$C_{16}$aralkyl or $C_6$–$C_{16}$aryl or $C_7$–$C_{16}$aralkyl which are substituted by halogen, cyano, $C_1$–$C_4$alkyl, $C_1$–$C_4$alkoxy, $C_1$–$C_4$haloalkyl or $C_1$–$C_4$cyanoalkyl, or $R_5$ and $R_6$ together are $C_4$–$C_5$alkylene or 3-oxapentalene, and $R_7$ is unsubstituted $C_1$–$C_6$alkyl or $C_1$–$C_6$alkyl substituted by —Oh, —$OR_{11}$ or —$SR_{11}$, —$NR_9R_{10}$, —COOH, —$COOR_7$, —$OCOR_{11}$, —$CONH_2$, —$CONHR_5$, —$CONR_5R_6$, halogen or cyano; is is $C_5$–$C_6$cycloalkyl, allyl, methallyl, propargyl unsubstituted phenyl or benzyl or phenyl or benzyl which is substituted by $C_1$–$C_4$alkyl, $C_1$–$C_4$alkoxy or halogen, wherein each of $R_9$ and $R_{10}$ individually is $C_1$–$C_6$alkyl, $C_5$–$C_6$cycloalkyl, phenyl or benzyl, or $R_9$ and $R_{10}$ together are $C_4$–$C_5$alkylene or 3-oxypentalene and $R_{11}$ is $C_1$–$C_6$alkyl, cyclohexyl or phenyl; or $R_3$ and $R_4$ taken together are —O— or —$NR_8$— wherein $R_8$ is hydrogen or $R_7$.

13. A 1-amino-1,4-dihydropropyridine-2,3-dicarboxylic acid derivative of formula IV according to claim 12, wherein $R_1$ is hydrogen, $R_2$ is ethyl, n-propyl, isopropyl or n-butyl, each of $R_9$ and $R_{10}$ is methyl and $R_3$ and $R_4$ together are a group of the formula

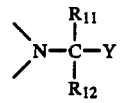

wherein $R_{11}$ is methyl, $R_{12}$ is isopropyl and Y is a cyano or a carbamoyl group.

14. A pyridine-2,3-dicarboxylic acid derivative of the formula Ia

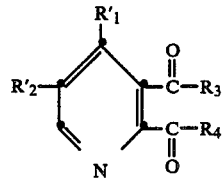

(Ia)

wherein
$R_1'$ is hydrogen,
$R_2'$ is $C_1$–$C_4$alkyl and
$R_3$ and $R_4$ together are a group of the formula

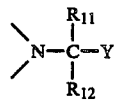

wherein
$R_{11}$ and $R_{12}$ are hydrogen or $C_1$–$C_6$alkyl and
Y is a cyano or a carbamoyl group.

* * * * *